(12) United States Patent
Kahn

(10) Patent No.: US 6,696,579 B2
(45) Date of Patent: Feb. 24, 2004

(54) ALKYLENE CARBONATE PURIFICATION

(75) Inventor: Andrew P. Kahn, Eagleville, PA (US)

(73) Assignee: Arco Chemical Technology, L.P., Greenville, DE (US)

( * ) Notice: Subject to any disclaimer, the term of this patent is extended or adjusted under 35 U.S.C. 154(b) by 81 days.

(21) Appl. No.: 10/141,617

(22) Filed: May 8, 2002

(65) Prior Publication Data
US 2003/0212280 A1 Nov. 13, 2003

(51) Int. Cl.[7] .............................................. C07D 317/00
(52) U.S. Cl. ....................................................... 549/449
(58) Field of Search ................ 549/449, 228, 549/230

(56) References Cited

U.S. PATENT DOCUMENTS

| 2,773,070 | A | | 12/1956 | Lichtenwalter et al. |
| 2,873,282 | A | | 2/1959 | McClellan |
| 4,786,741 | A | | 11/1988 | Sachs |
| 5,179,214 | A | | 1/1993 | Marquis et al. |
| 5,283,356 | A | | 2/1994 | Marquis et al. |
| 5,405,977 | A | * | 4/1995 | Cuscurida et al. ........... 549/541 |
| 5,631,386 | A | | 5/1997 | Gupta |
| 6,384,240 | B1 | * | 5/2002 | Machac et al. ............. 549/230 |
| 6,387,223 | B1 | | 5/2002 | Marquis et al. |

FOREIGN PATENT DOCUMENTS

WO    WO 01/66510 A2    9/2001

* cited by examiner

Primary Examiner—Alan L. Rotman
Assistant Examiner—Robert Shiao
(74) Attorney, Agent, or Firm—William C. Long

(57) ABSTRACT

An alkylene carbonate such as propylene carbonate is contacted with an alumina or silica solid adsorbent having a surface area of 50–400 $m^2/g$ such as basic alumina to remove impurities therefrom and improve color and color stability.

5 Claims, No Drawings

ALKYLENE CARBONATE PURIFICATION

BACKGROUND OF THE INVENTION

1. Field of the Invention

The present invention relates to the purification of an alkylene carbonate such as propylene carbonate by contact with a solid adsorbent such as basic alumina having a surface area of 50–400 m$^2$/gram.

2. Description of the Prior Art

It is known to form an alkylene carbonate by the reaction of an alkylene oxide with carbon dioxide. See, for example, U.S. Pat. Nos. 2,773,070, 2,873,282, 4,786,741, 5,179,214, 5,283,356 and the like. Appropriate catalyst and reaction conditions are known and taught for example, in the above references.

A problem which has been associated with prior practices has been the color instability of the product alkylene carbonate as well as contamination of the product alkylene carbonate with various impurities.

It has been proposed, for example in U.S. Pat. Nos. 5,179,214 and 5,282,356 that in a continuous reaction system the alkylene oxide and carbon dioxide be introduced into a continuous reactor containing catalyst with continuous recirculation of a portion of the reaction mixture and continuous withdrawal and flashing of another portion of the reaction mixture to remove unreacted alkylene oxide and carbon dioxide; the removed materials can be compressed and returned to the reaction mixture. The residue from flashing is distilled to separate product carbonate from the catalyst solution. A problem in continuous systems has been that higher temperatures are employed than in batch systems in order to reduce unreacted alkylene oxide levels but this has the disadvantage of forming light and heavy impurities. Elaborate alkylene oxide distillation procedures are required to produce satisfactory product.

In U.S. Pat. No. 5,631,386 it is proposed to remove residual alkylene oxide from the alkylene carbonate by stripping with an inert gas such as carbon dioxide.

WO 01/66510 A2 describes a process to provide high purity alkylene carbonate through use of multiple distillations. It is disclosed that the high purity alkylene carbonate may be further purified by use of high surface area carbon to improve the UV absorbance of the alkylene carbonate. However, unlike the process of this invention, the process of WO 01/66510 A2 is not effective for the removal of catalyst residues.

BRIEF DESCRIPTION OF THE INVENTION

It has now been found that color forming impurities including nitrogen and bromine compounds derived from the catalyst used to produce the alkylene carbonate can be removed from the alkylene carbonate by contact with a high surface area alumina or silica.

DETAILED DESCRIPTION

Alkylene carbonates treated by the invention, are prepared using known reagents, catalysts and reaction conditions. See, for example, U.S. Pat. Nos. 2,773,282, 2,773,070, 2,873,282, 4,786,741, 5,179,214, 5,283,356 and the like, the disclosures of which are incorporated herein by reference.

The invention is especially applicable to the treatment of propylene carbonate and ethylene carbonate prepared by the tetraethyl ammonium bromide catalyzed reaction of propylene oxide with carbon dioxide and ethylene oxide with carbon dioxide.

As described in U.S. Pat. No. 5,283,356, the reaction of an alkylene oxide and carbon dioxide to form alkylene carbonate may be carried out at a temperature of from about 100° to about 225° C. or higher, preferably from about 175° to about 215° C. The reaction may be carried out at atmospheric pressure or, advantageously, under a pressure of about 300 psig or greater. More preferably, the reaction is carried out under a pressure of about 300 to about 3000 psig. The reaction may be conducted either batch-wise or continuously.

In a continuous reaction, the alkylene oxide and carbon dioxide are introduced to a continuous reactor containing the catalyst, from which a portion of the reaction mixture may be continuously recirculated through the reactor. Another portion of this reaction mixture is continuously withdrawn and treated to remove unreacted alkylene oxide from product alkylene carbonate. Alternatively, the continuous reaction can be carried out on a once through basis with suitable heat removal.

Alternatively, batches of the alkylene oxide and catalyst may be introduced into an autoclave or kettle type reactor. The desired pressure may be built up by introducing carbon dioxide. Typically, the reaction mixture is heated to reaction temperature, agitated, and held under a super atmospheric pressure of carbon dioxide. After the bulk of the alkylene oxide has reacted, the reaction mixture can be treated to remove unreacted alkylene oxide.

The alkylene oxide and carbon dioxide should be mixed in proportion to provide an excess of carbon dioxide over and above the stoichiometric amount required for reaction. This excess may be on the order of from about 1.1 moles of carbon dioxide per mole of alkylene oxide to about 10 moles of carbon dioxide per mole of alkylene oxide. An excess of alkylene oxide should be avoided, because it results in undesired by-products, chiefly alkylene oxide polymer, and because explosive conditions may result.

After completion of the desired reaction between the alkylene oxide and carbon dioxide to form alkylene carbonate, the reaction mixture is treated to remove residual unreacted alkylene oxide. Advantageously, the system pressure is reduced and carbon dioxide and alkylene oxide are vented from the system. Even after such venting the reaction mixture contains unacceptable levels of alkylene oxide, usually from 0.1% to 1% or more as against acceptable levers 0.06% or less. Simple flashing and removal of flashed alkylene oxide and carbon dioxide is generally ineffective in producing acceptable product. The stripping procedure of U.S. Pat. No. 5,631,386 can advantageously be used.

Alkylene carbonates prepared by the above known procedures tend to develop discoloration and this has an important and adverse effect on the sale and use of such products. Although the exact cause of the color instability is not known with certainty, it is believed that at least a factor contributing to the color instability is the presence in the alkylene carbonate of small amounts of nitrogen and/or halide compounds derived from the catalyst used in production of the alkylene carbonate and art important feature of the invention is the removal of such impurities.

Now, in accordance with the present invention, in order to reduce the level of impurities such as nitrogen compounds and to improve the color and color stability of an alkylene carbonate, the carbonate is contacted in the liquid phase with a high surface area silica or alumina adsorbent effective to improve color and reduce the impurities level of the carbonate. Adsorbents used in practice of the invention have a surface area of 50 to 400 m$^2$/g. Basic alumina is useful as are conventional silica and alumina having the designated surface area.

The adsorptive contact is conveniently carried out at temperatures in the range of about 15° C. to 90° C., preferably 20° C. to 40° C. Flow rates of about 1 to 10 volumes of alkylene carbonate per volume of adsorbent per hour, preferably 2 to 5 are preferred.

It is generally preferred to employ plural adsorbent contact beds so that a depleted bed can be regenerated while a fresh bed is used. Regeneration can be by washing as with water followed by drying or by stripping with a heated insert gas such as steam, nitrogen or the like.

Basic alumina as used herein refers to alumina having a surface area of 50–400 m$^2$/g which has been impregnated with a basic solution having a pH of at least 9 and dried. The basic solution may suitably be a solution of an alkali metal or ammonium compound such as one selected from hydroxides, carbonates, bicarbonates, phosphates, and organic acid salts. Suitable basic compounds that may be employed include sodium, potassium or ammonium carbonate, hydroxide, bicarbonate, nitrate, formate, acetate, benzoate or citrate.

The most preferred basic compound for use is potassium carbonate.

A modified alumina for use in the invention may be prepared by making a solution of the chosen basic compound having an appropriate pH as described above and adding the solution to an alumina in a volume just sufficient to fill the pores of the alumina without producing surface wetness. The concentration and the amount of the solution may be chosen to produce a loading of the compound on the alumina of from 1 to 10% on a dry weight basic.

In addition to basic alumina as described above, conventional alumina and silica having the designated surface area can be employed.

The following examples illustrates the invention, and the APHA (American Public Health Association) color standard is used as a color measuring unit:

EXAMPLE 1

A 1 cm ID column was packed with Aldrich basic alumina (150 mesh) (38.4 g, 50 cc, SA=155 m$^2$/g). A feed of propylene carbonate (APHA=431, 1400 ppm Br and 250 ppm N) was passed through the bed at a LHSV of 2/hr and product was collected in 50 cc cuts. The following results were obtained:

TABLE 1

| Cut # | APHA Color | % N Removed | % Br Removed |
|---|---|---|---|
| 1 | 45 | 99 | 98 |
| 2 | 110 | 98 | 93 |
| 3 | 348 | 40 | 36 |
| 4 | 272 | 4 | 0 |

The above results demonstrate the effectiveness of the adsorption treatment of the present invention in improving color and reducing impurities content of propylene carbonate.

In addition, accelerated aging tests showed that color did not develop even after 2 months at 50° C.

EXAMPLE 2

A 1 cm ID column was packed with Aldrich acidic alumina (150 mesh) (46.6 g, 49 cc, SA=155 m$^2$/g). A feed of propylene carbonate (APHA=431, 1020 ppm Br and 180 ppm N) was passed through the bed at a LHSV of 1/hr and product was collected in 50 cc cuts. The following results were obtained:

TABLE 2

| Cut # | APHA Color | % N Removed | % BR Removed |
|---|---|---|---|
| 1 | 32 | 99 | 93 |
| 2 | 76 | >99 | 94 |

EXAMPLE 3

A 1 cm ID column was packed with Aldrich neutral alumina (150 mesh) 44.3 g, 47 cc, SA=155 m$^2$/g). A feed of propylene carbonate (APHA=431, 1020 ppm Br and 180 ppm N) was passed through the bed at a LHSV of 2/hr and product was collected in 50 cc cuts. The following results were obtained:

TABLE 3

| Cut # | APHA Color | % N Removed | % Br Removed |
|---|---|---|---|
| 1 | 35 | >99 | 94 |
| 2 | 85 | >99 | 95 |
| 3 | 221 | 79 | 71 |
| 4 | 230 | 22 | 12 |

EXAMPLE 4

A 1 cm ID column was packed with Engelhard A13996R Alumina (14×30 mesh) (23.4 g, 46 cc, SA=196 m$^2$/g). A feed of propylene carbonate (APHA=431, 1020 ppm Br and 180 ppm N) was passed through the bed at a LHSV of 2/hr and product was collected in 50 cc cuts. The following results were obtained:

TABLE 4

| Cut # | APHA Color | % N Removed | % Br Removed |
|---|---|---|---|
| 1 | 127 | 96 | 91 |
| 2 | 219 | 82 | 71 |
| 3 | 265 | 56 | 41 |
| 4 | 296 | 39 | 22 |

EXAMPLE 5

A 1 cm ID column was packed with Grace silica (14×30 mesh) (16.3 g, 44 cc, SA=320 m$^2$/g). A feed of propylene carbonate (APHA)=431, 1020 ppm Br and 180 ppm N) was passed through the bed at a LHSV of 2/hr and product was collected in 50 cc cuts. The following results were obtained:

TABLE 5

| Cut # | APHA Color | % N Removed | % Br Removed |
|---|---|---|---|
| 1 | 99 | 98 | 90 |
| 2 | 154 | >99 | 80 |
| 3 | 231 | 92 | 80 |
| 4 | 308 | 17 | 71 |

EXAMPLE 6

A 1 cm ID column was packed with Engelhard E149T alumina (14×30 mesh) (29.3 g, 44 cc, SA=50 m$^2$/g). A feed of propylene carbonate (APHA=431, 1020 ppm Br and 180 ppm N) was passed through the bed at a LHSV of 2/hr and product was collected in 50 cc cuts. The following results were obtained:

TABLE 6

| Cut # | APHA Color | % N Removed | % Br Removed |
|---|---|---|---|
| 1 | 187 | 83 | 71 |
| 2 | 317 | 22 | 12 |
| 3 | 348 | 6 | 2 |
| 4 | 363 | 6 | 2 |

Comparative Example 1 (low surface area alumina)

A 1 cm ID column was packed with Alcoa T64 alumina (90.8 g, 47 cc, SA=0.04 $m^2/g$). A feed of propylene carbonate (APHA=430, 1020 ppm Br) was passed through the bed at a LHSV of 2/hr and product was collected in 50 cc cuts. The following results were obtained:

Comparative Table 1

| Cut # | APHA Color | % N Removed | % Br Removed |
|---|---|---|---|
| 1 | 409 | 0 | 2 |
| 2 | 413 | 6 | 2 |
| 3 | 413 | 0 | 2 |
| 4 | 411 | 0 | 2 |

Comparative Example 2 (activated carbon)

A 1 cm ID column was packed with Calgon CAL 12×40 Carbon (14.0 g, 41 cc, SA=1100 $m^2/g$). A feed of propylene carbonate (APHA=430, 1020 ppm Br) was passed through the bed at a LHSV of 2/hr and product was collected in 50 cc cuts. The following results were obtained:

Comparative Table 2

| Cut # | APHA Color | % N Removed | % Br Removed |
|---|---|---|---|
| 1 | 43 | 39 | 31 |
| 2 | 71 | 28 | 12 |
| 3 | 104 | 22 | 12 |
| 4 | 119 | 17 | 12 |

Comparative Example 3 (activated carbon)

A 1 cm ID column was packed with Calgon APC 12×40 Carbon (14.0 g, 41 cc, SA=1350 $m^2/g$). A feed of propylene carbonate (APHA=430, 1020 ppm Br) was passed through the bed at a LHSV of 2/hr and product was collected in 50 cc cuts. The following results were obtained:

Comparative Table 3

| Cut # | APHA Color | % N Removed | % Br Removed |
|---|---|---|---|
| 1 | 53 | 39 | 31 |
| 2 | 82 | 28 | 12 |
| 3 | 114 | 17 | 12 |
| 4 | 126 | 22 | 12 |

The above data show the effective results according to the invention as well as the comparative ineffectiveness of low surface area adsorbents and high surface area carbon by comparison.

I claim:

1. The method of treating an alkylene carbonate selected from ethylene carbonate and propylene carbonate which comprises contacting the alkylene carbonate in the liquid phase with a silica or alumina solid adsorbent having a surface area of 50–400 $m^2/g$ at conditions effective to improve the color and color stability of the alkylene carbonate by reducing the APHA color of the alkylene carbonate to below about 200, and removing a predominance of bromine and nitrogen impurities therefrom.

2. The method of claim 1 wherein the alkylene carbonate is propylene carbonate.

3. The method of claim 1 wherein the solid adsorbent is alumina.

4. The method of claim 1 wherein the solid adsorbent is basic alumina.

5. The method of treating an alkylene carbonate selected from ethylene carbonate and propylene carbonate which comprises contacting the alkylene carbonate in the liquid phase with a silica solid adsorbent having a surface area of 50–400 $m^2/g$ at conditions effective to improve the color and color stability of the alkylene carbonate by reducing the APHA color of the alkylene carbonate to below about 200, and removing a predominance of bromine and nitrogen impurities therefrom.

* * * * *